(12) United States Patent
Ammannati et al.

(10) Patent No.: US 7,445,777 B2
(45) Date of Patent: Nov. 4, 2008

(54) ENZYMATIC TREATMENT OF RETINITIS PIGMENTOSIS

(76) Inventors: Paola Ammannati, Via E. Zerboglio, 8, 56125 - Pisa (IT); Roberto Giordani, Via V. Nisi, 2, 56125 - Pisa (IT)

( * ) Notice: Subject to any disclaimer, the term of this patent is extended or adjusted under 35 U.S.C. 154(b) by 278 days.

(21) Appl. No.: 10/530,067

(22) PCT Filed: Oct. 1, 2002

(86) PCT No.: PCT/IT02/00624

§ 371 (c)(1),
(2), (4) Date: Mar. 31, 2005

(87) PCT Pub. No.: WO2004/030693

PCT Pub. Date: Apr. 15, 2004

(65) Prior Publication Data

US 2006/0134088 A1    Jun. 22, 2006

(51) Int. Cl.
*A61K 38/54*    (2006.01)
*A61F 2/00*    (2006.01)
*C12Q 1/68*    (2006.01)

(52) U.S. Cl. .................. 424/94.3; 424/94.1; 424/427; 435/6

(58) Field of Classification Search ............ None
See application file for complete search history.

(56) References Cited

FOREIGN PATENT DOCUMENTS

| FR | 2784030 | 4/2000 |
| FR | 2784898 | 4/2000 |

OTHER PUBLICATIONS

Carmody et al. (1999) Reactive Oxygen Species as Mediators of Photoreceptor Apoptosis in Vitro. Experimental Cell Research 248(2): 520-530.*
Ahuja-Jensen et al. (2007) Low glutathione peroxidase in rdl mouse retina increases oxidative stress and proteases. NeuroReport 18(8): 797-801.*
Ling-Hua Zeng et al., "Genetic Study of Retinitis Pigmentosa in China", *Ophthalmologica*, vol. 194, No. 1, 1987, pp. 34-39.
E.M. Gloria et al., "The Pathogenesis of Retinitis Pigmentosa. A Pilot Study on the Clinical Fluoroangiographic and Enzymatic Effect of Bendazac Lysine", *Bollettino di Oculistica*, vol. 69, No. 2, 1990, pp. 309-318.

* cited by examiner

*Primary Examiner*—Lisa J Hobbs
(74) *Attorney, Agent, or Firm*—Pollack, P.C.

(57) ABSTRACT

A pharmaceutical kit for treatment of retinitis pigmentosis and a method of producing the same, the kit comprising the enzymes glutathione peroxidase, prolidase, glucose-6-phosphate dehydrogenase and, optionally, aldose reductase in aliquot parts and interactive quantities appropriate for administering the enzymes in accordance with a predetermined time sequence.

8 Claims, No Drawings

ENZYMATIC TREATMENT OF RETINITIS PIGMENTOSIS

FIELD OF THE INVENTION

The present invention relates generally to the field of medicine and, more particularly, to the treatment of retinitis pigmentosis and the like.

BACKGROUND OF THE INVENTION

Retinitis pigmentosis is a disease of the retina that has many different pathological manifestations. Notably, it not only causes restriction of a patient's field of vision, but also increased difficulty in adapting to the dark and to penumbra, when it affects the peripheral zones of the retina. Generally speaking, this is because the peripheral zones accommodate a greater part of the rod cells that make vision in penumbra and perception of movement in the lateral zones possible. Alternatively or concurrently, retinitis pigmentosis may lead to loss of central vision, when the cone cells are the ones that are affected by the disease and, thereby, undergo deterioration. The rate at which the illness progresses varies from one patient to another. Overall, however, retinitis pigmentosis is an insidious disease that most often manifests itself in youth, especially children.

The cause(s) of this infirmity are presently unknown and there is not yet a cure. The only information known for certain about the disease concerns its possible genetic origin. More particularly, retinitis pigmentosis is believed to be passed, in part, by heredity from generation to generation, following mechanisms known to geneticists. Most forms of retinitis pigmentosis are hereditary and three transmission modalities have been identified thus far: dominantly autosomal, recessively autosomal and X-linked or bound by sex.

The main symptoms of the disease are crepuscular and nocturnal blindness, i.e., difficulty of seeing when lighting conditions are poor, and problems adapting from well-lit to dark environments or vice versa. This phenomenon is due to the fact that, at least in a majority of cases, attack in the early development phases of the illness is concentrated on the rod cells. Other common symptoms are a reaction to excessively strong light, a gradual narrowing of the visual field, which manifests itself in the form of difficulty in perceiving objects situated to either side of the patient, or stumbling over steps or other low obstacles, eventually resulting in complete blindness.

The course followed by the illness is of extremely variable duration, but is always gradual and ultimately leads to disability. In the greater part of cases, however, the symptoms described previously become aggravated, the visual field becomes more and more restricted and eventually closes completely. Other complaints tend to appear, dazzlement being among them, as well as the inability to distinguish colors, and a particular form of cataract. In many cases, the final outcome is, unfortunately, total blindness.

In diagnosing retinitis pigmentosis, it is common to rely on tests such as examination of the fundus of the eye, examination of the visual field, electroretinograms, fluorangiography, and visus examination:

the fundus of the eye is examined to assess the condition of the retina and to look for the presence of pigment spots on the retinal surface characteristic of the illness, which assume an "osteoblast-like" appearance. It is noted that some rare forms of retinitis pigmentosis are not characterized by spots on the fundus of the eye, though they present the same symptoms otherwise;

examination of the visual field makes it possible to evaluate the sensitivity of various parts of the retina to light stimuli. It is considered particularly useful to have objective documentation of the difficulty in visual perception experienced by the patient;

an electroretinogram (ERG) records the electrical activity of the retina in response to particular light stimuli, thereby enabling the functionality of the two different types of photoreceptors (i.e. cone cells and rod cells) to be evaluated. The electroretinogram is very important for diagnosing retinitis pigmentosis, because—even when the illness is in its initial stages—the resulting trace almost always is either very flat or absent altogether;

fluorangiography is performed by intravenous injection of a fluorescent substance and subsequent photography of the retina at different times. As a result of blood circulation, the fluorescent substance arrives at the retina, where it colours the arteries, the capillaries and the veins, rendering them and the functional state of their walls visible;

visus examination allows visual acuity to be evaluated and involves the patient's reading of letters having different sizes at a distance of about three meters.

Although retinitis pigmentosis was identified and classified as a disease more than fifty (50) years ago, little concrete progress has been achieved thus far, either with respect to possible cures or equally important on the front of understanding the causes that determine and regulate its course. Currently, the most widely followed research internationally are: (i) the genetic approach, which seeks to identify the gene or genes responsible for the illness for subsequent intervention through modern genetic engineering techniques; (ii) the transplant approach, an objective of which is to perfect a technique that would make it possible to transplant retinal tissue or, at least, graft healthy cells into diseased retinas; and (iii) the immunological approach, which develops and investigates theories that what underlies the illness is some alteration of the immunological system.

OBJECTS AND SUMMARY OF THE INVENTION

Accordingly, it is an object of the present invention to provide a pharmacological composition in the form of a kit for effective and efficient treatment of retinitis pigmentosis.

Another object of the present invention is to provide a method of treating retinitis pigmentosis that allows gradual recovery of visual acuity and enlargement of the field of vision, the sharpness of images, the perception of colors, and the resurrection of a normal electroretinogram over time.

According to one aspect of the present invention, selected enzymes are incorporated in a pharmaceutical composition for treating retinitis pigmentosis by injecting the enzyme incorporated composition into the retrobulbar tissue, of a patient's eye.

According to another aspect of the present invention, there is provided a pharmaceutical kit for treatment of retinitis pigmentosis which comprises the enzymes glutathione peroxidase (Enzyme A), prolidase (Enzyme B), glucose-6-phosphate dehydrogenase (Enzyme C) and, optionally, aldose reductase (Enzyme D) in aliquot parts and interactive quantities appropriate for administering: (i) Enzyme A at a concentration generally within a range of 0.03 U.I. and 0.05 U.I. in about 0.4 ml of physiological solution for approximately three consecutive days, at monthly intervals, for about three months and for each eye; (ii) Enzyme B, starting from the month following the last administration of Enzyme A, at a concentration generally within a range of 5 U.I. and 7 U.I. in about 0.4 ml of physiological solution for approximately three consecutive days, at monthly intervals, for about three months and for each eye; (iii) Enzyme C, starting from the month following the last administration of Enzyme B, at a concentration generally within a range of 7 U.I. and 9 U.I. in about 0.4 ml of physiological solution for approximately three consecutive days, at monthly intervals, for about three months and for each eye; (iv) Enzyme D, starting from the month following the last administration of Enzyme C, at a concentration generally within a range of 5 U.I. and 7 U.I. in about 0.4 ml of physiological solution for approximately three consecutive days, at monthly intervals, for about three months and for each eye.

In accordance with a further aspect of the present invention, a method is provided for producing a pharmaceutical kit which comprises the enzymes glutathione peroxidase (Enzyme A), prolidase (Enzyme B), glucose-6-phosphate dehydrogenase (Enzyme C) and, optionally, aldose reductase (Enzyme D) for treatment of retinitis pigmentosis by injection into a patient's retrobulbar tissue, the method comprising the steps of providing the enzymes in aliquot parts and in interactive quantities appropriate for administering: (i) Enzyme A at a concentration generally within a range of 0.03 U.I. and 0.05 U.I. in about 0.4 ml of physiological solution for approximately three consecutive days, at monthly intervals, for about three months and for each eye; (ii) Enzyme B, starting from the month following the last administration of Enzyme A, at a concentration generally within a range of 5 U.I. and 7 U.I. in about 0.4 ml of physiological solution for approximately three consecutive days, at monthly intervals, for about three months and for each eye; (iii) Enzyme C, starting from the month following the last administration of Enzyme B, at a concentration generally within a range of 7 U.I. and 9 U.I. in about 0.4 ml of physiological solution for approximately three consecutive days, at monthly intervals, for about three months and for each eye; and (iv) Enzyme D, starting from the month following the last administration of Enzyme C, at a concentration generally within a range of 7 U.I. and 9 U.I. in about 0.4 ml of physiological solution for approximately three consecutive days, at monthly intervals, for about three months and for each eye.

DETAILED DESCRIPTION OF THE PREFERRED EMBODIMENTS

A specific, illustrative enzymatic treatment of retinitis pigmentosis and a kit that includes a pharmaceutical composition for treating the same are provided, according to various aspects of the present invention. More particularly, according to one embodiment of the present invention, one or more selected enzymes are administered in accordance with a predetermined time sequence and selected modalities. Preferably, these enzymes include glutathione peroxidase (hereinafter referred to as Enzyme A), prolidase (hereinafter referred to as Enzyme B), glucose-6-phosphate-dehydrogenase (hereinafter referred to as Enzyme C).

Optionally, the treatment also uses aldose reductase (hereinafter referred to as Enzyme D), which has been found beneficial when the patient complains of visual fogging, as often occurs during the course of the disease.

The enzymes employed in treatments, according to the present inventions, are available commercially in lyophilized form. These enzymes are preferably dissolved in physiological solution in order to make them available in the patient's body upon treatment.

Each enzyme—in the form of enzyme solution—is desirably administered by retrobulbar injection into each eye for three consecutive days, repeating the administration on another two occasions, each separated from its predecessor by a period of one month (for each enzyme). In practice, the procedure is as follows:

one dose of Enzyme A is injected into the retrobulbar tissue of each eye for three consecutive days at the beginning of treatment, the treatment being repeated in the second and third month;

in the fourth, fifth and sixth month, one dose of Enzyme B is injected into the retrobulbar tissue of each eye for three consecutive days;

in the seventh, eighth and ninth month, one dose of Enzyme C is injected into the retrobulbar tissue of each eye for three consecutive days;

if necessary, in the next three months and for three days in each month, the treatment is then continued with Enzyme D, the administration mode being exactly as before.

The doses of the various enzymes used for each injection i.e., in each eye) are as follows:

| | |
|---|---|
| Enzyme A | 0.03-0.05 U.I. |
| Enzyme B | 5-7 U.I. |
| Enzyme C | 7-9 U.I. |
| Enzyme D | 7-9 U.I. |

The preferred doses of the various enzymes upon each injection are as follows:

| | |
|---|---|
| Enzyme A | 0.04 U.I. |
| Enzyme B | 6.67 U.I. |
| Enzyme C | 8.00 U.I. |
| Enzyme D | 8.00 U.I. |

Generally speaking, these doses remain the same for all patients, independently of the typology of the alteration. In particular, the enzyme solutions are prepared such that the quantities indicated above may be part of an injection of about 0.4 ml of physiological solution. For example, the kit of enzyme solutions suitable for providing injectable doses of about 0.4 ml with the preferred enzyme quantities set forth above are desirably prepared as follows:

Enzyme A:

Phial comprising approximately 10 U.I. of lyophilized enzyme, up to about 100 ml in physiological solution.

Enzyme B:

Phial comprising around 1000 U.I. of lyophilized enzyme, up to about 60 ml in physiological solution.

Enzyme C:

Phial comprising around 2000 U.I. of lyophilized enzyme, up to approximately 100 ml in physiological solution.

Enzyme D:

Phial comprising about 2000 U.I. of lyophilized enzyme, up to roughly 100 ml in physiological solution.

As those skilled in the art will appreciate, the ratios may need to be modified if the dose of any one of the enzymes within its dosing range is changed. The enzymes are desirably administered in the order set forth above, and the injection cycles are to be continued without interruption.

Turning now to the kit used for treating retinitis pigmentosis, in accordance with the present invention, it includes the aforementioned enzymes in aliquot parts and interactive quantities appropriate for administering:

a) Enzyme A at a concentration generally within a range of 0.03 U.I. and 0.05 U.I. in about 0.4 ml of physiological solution for three consecutive days, at monthly intervals, for three consecutive days and for each eye;

b) Enzyme B, starting from the month following the last administration of enzyme A, at a concentration between about 5 U.I. and about 7 U.I. in approximately 0.4 ml of physiological solution for three consecutive days, at monthly intervals, for three months and for each eye;

c) Enzyme C, starting from the month following the last administration of Enzyme B, at a concentration generally within a range of 7 U.I. and 9 U.I. in about 0.4 ml of physiological solution for three consecutive days, at monthly intervals, for three months and for each eye.

Optionally, the kit may also include Enzyme D, to be administered, starting from the month following the last administration of Enzyme C, at a concentration of about 5 U.I. to about 7 U.I. in around 0.4 ml of physiological solution for three consecutive days, at monthly intervals, for three months and for each eye.

More specifically, the enzymes of each kit are in lyophilized form and in quantities sufficient for at least one complete series of administrations, each enzyme being subdivided into aliquot parts containing a quantity sufficient for one three-month injection cycle, i.e., eighteen injections, or for one daily administration, i.e., two injections, and optionally the appropriate doses of physiological solution comprising the aliquot parts. In particular, in each kit, the various enzymes are subdivided into one or more aliquot parts, each comprising, in the preferred dosage forms set forth above, between about 0.04 U.I and about 0.72 U.I of Enzyme A, from about 6.67 U.I. to about 120 U.I. of Enzyme B, generally within a range of 8 U.I and 144 U.I of Enzyme C and possibly from around 8 U.I to around 144 U.I. of Enzyme D. It is noted that three or more aliquot parts of physiological solution from approximately 0.4 ml to roughly 7.2 ml each may also be present.

Patients subjected to treatment, in accordance with the present invention, experienced a gradual improvement in their visual acuity and field of vision, color perception and image sharpness (definition). Their electroretinograms improved little by little, eventually being restored over time. The treatment administered produced a positive response in all patients, albeit over different periods of time. Follow-up checks with the patients after 5-8 years demonstrated that the improvements achieved are permanent and have not revealed any side effects.

Some experimental data confirms the hypothesis that retinitis pigmentosis may be due to an enzyme defect that alters the metabolism of the retina, modifying not only the vision process, but also facilitating the accumulation of pigment, a characteristic feature of the illness.

Studies carried out on rabbits (New Zealand/Fulvo di Borgogna) have shown that complete inhibition of some enzymes causes variations in their electroretinograms, with reduction in the depolarization wave to the point of extinction and restoration of a normal trace after retrobulbar administration of glutathione peroxidase (Enzyme A) and prolidase (Enzyme B). Erythrocyte level reduction in glucose-6-phosphate dehydrogenase and glutathi-one peroxidase with patients affected by retinitis pigmentosis was demonstrated subsequently by a comparison of their enzyme erythrocyte concentrations with those of subjects not affected by the illness, seemingly in good health, the two groups being homogeneous in sex and age.

The invention claimed is:

1. A pharmaceutical kit for treatment of retinitis pigmentosis which comprises the enzymes glutathione peroxidase (Enzyme A), prolidase (Enzyme B), glucose-6-phosphate dehydrogenase (Enzyme C) and, optionally, aldose reductase (Enzyme D) in aliquot parts and interactive quantities appropriate for administering:

a) Enzyme A at a concentration generally within a range of 0.03 U.I. and 0.05 U.I. in about 0.4 ml of physiological solution for approximately three consecutive days, at monthly intervals, for about three months and for each eye;

b) Enzyme B, starting from the month following the last administration of Enzyme A, at a concentration generally within a range of 5 U.I. and 7 U.I. in about 0.4 ml of physiological solution for approximately three consecutive days, at monthly intervals, for about three months and for each eye;

c) Enzyme C, starting from the month following the last administration of Enzyme B, at a concentration generally within a range of 7 U.I. and 9 U.I. in about 0.4 ml of physiological solution for approximately three consecutive days, at monthly intervals, for about three months and for each eye; and d) Enzyme D, starting from the month following the last administration of Enzyme C, at a concentration generally within a range of 7 U.I. and 9 U.I. in about 0.4 ml of physiological solution for approximately three consecutive days, at monthly intervals, for about three months and for each eye.

2. The kit set forth in claim 1, wherein the concentration of Enzyme A is about 0.04 U.I. in approximately 0.4 ml of physiological solution, the concentration of Enzyme B is about 6.67 U.I. in approximately 0.4 ml of physiological solution and the concentration of Enzyme C is about 8 U.I. in around 0.4 ml of physiological solution, the concentration of optional Enzyme D being equal to about 8 U.I. in approximately 0.4 ml of physiological solution.

3. The kit set forth in claim 1, wherein the kit further comprises the enzymes in lyophilized form, in quantities sufficient for at least one series of administrations of from a) to c) and, optionally, also d), subdivided into aliquot parts containing, for each enzyme, a selected quantity of enzyme sufficient for the constitution of the aliquot parts.

4. A kit set forth in claim 1, wherein the kit further comprises the enzymes in lyophilized form subdivided into one or more aliquot parts, each containing from about 0.04 U.I. to about 0.72 U.I. of Enzyme A, from about 0.67 U.I. to around 120 U.I. of Enzyme B, from approximately 8 U.I. to about 144 U.I. of Enzyme C and, optionally, from around 8 U.I. to about 144 U.I. of Enzyme D, and, optionally, three or more aliquot parts of physiological solution generally within a range of 0.4 ml and 7.2 ml each.

5. A method of producing a pharmaceutical kit which includes the enzymes glutathione peroxidase (Enzyme A), prolidase (Enzyme B), glucose-6-phosphate dehydrogenase (Enzyme C) and, optionally, aldose reductase (Enzyme D) for treatment of retinitis pigmentosis by injection into a patient's retrobulbar tissue, the method comprising the steps of providing the enzymes in aliquot parts and in interactive quantities appropriate for administering:

a) Enzyme A at a concentration generally within a range of 0.03 U.I. and 0.05 U.I. in about 0.4 ml of physiological solution for approximately three consecutive days, at monthly intervals, for about three months and for each eye;

b) Enzyme B, starting from the month following the last administration of Enzyme A, at a concentration generally within a range of 5 U.I. and 7 U.I. in about 0.4 ml of physiological solution for approximately three consecutive days, at monthly intervals, for about three months and for each eye;

c) Enzyme C, starting from the month following the last administration of Enzyme B, at a concentration generally within a range of 7 U.I. and 9 U.I. in about 0.4 ml of physiological solution for approximately three consecutive days, at monthly intervals, for about three months and for each eye; and d) Enzyme D, starting from the month following the last administration of Enzyme C, at a concentration generally within a range of 7 U.I. and 9 U.I. in about 0.4 ml of physiological solution for approximately three consecutive days, at monthly intervals, for about three months and for each eye.

6. The method set forth in claim 5, wherein concentration of Enzyme A is about 0.04 U.I. in approximately 0.4 ml of physiological solution, the concentration of Enzyme B is about 6.67 U.I. in around 0.4 ml of physiological solution and the concentration of Enzyme C is approximately 8 U.I. in about 0.4 ml of physiological solution, the concentration of optional Enzyme D being equal to about 8 U.I. in about 0.4 ml of phisiological solution.

7. The method set forth in claim 5, wherein the kit further comprises the enzymes in lyophilized form, in quantities sufficient for at least one series of administrations of from a) to c) and, optionally, also d), subdivided into aliquot parts including, for each enzyme, a quantity of enzyme sufficient for the constitution of the aliquot parts.

8. The method set forth in claim 5, wherein the kit further comprises the enzymes in lyophilized form subdivided into one or more aliquot parts, each having generally within a range of 0.04 U.I. and 0.72 U.I. of Enzyme A, from about 0.67 U.I. to about 120 U.I. of Enzyme B, from about 8 U.I. to about 144 U.I. of Enzyme C and, optionally, from about 8 U.I. to about 144 U.I. of Enzyme D, and, optionally, three or more aliquot parts of physiological solution generally within a range of 0.4 ml and 7.2 ml each.

* * * * *